United States Patent
Schamper et al.

(10) Patent No.: US 6,403,067 B1
(45) Date of Patent: Jun. 11, 2002

(54) STABLE EMULSIONS FOR COSMETIC PRODUCTS

(75) Inventors: Thomas Schamper, Cranbury; Suman Kumar Chopra, Dayton; Bhal Moghe, Whitehouse Station; John Carl-Frederick Brahms, Piscataway; Mardoqueo Bustos, Hillsborough; Peter Hilliard, Jr., Far Hills; Marie Johansson, Watchung; Claudo Ortiz, Dayton; Christine Popoff, Mornganville, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/575,483

(22) Filed: May 19, 2000

(51) Int. Cl.$^7$ ................................................ A61K 7/32
(52) U.S. Cl. ............................ 424/65; 424/401; 424/68
(58) Field of Search ............................ 424/65, 401, 68

(56) References Cited

U.S. PATENT DOCUMENTS

| | | | |
|---|---|---|---|
| 3,979,510 A | 9/1976 | Rubino | 424/47 |
| 4,021,536 A | 5/1977 | Rubino | 424/47 |
| 4,673,570 A | 6/1987 | Soldati | 424/66 |
| 4,900,542 A | 2/1990 | Parrotta, Jr. et al. | 424/66 |
| 4,980,156 A | 12/1990 | Raleigh et al. | 424/66 |
| 5,008,103 A | 4/1991 | Raleigh et al. | 424/66 |
| 5,216,033 A | 6/1993 | Pereira et al. | 514/844 |
| 5,292,503 A | 3/1994 | Raleigh et al. | 424/59 |
| 5,401,870 A | 3/1995 | Raleigh et al. | 556/445 |
| 5,463,098 A | 10/1995 | Giovanniello et al. | 556/27 |
| 5,587,173 A | 12/1996 | Junino et al. | 424/401 |
| 5,599,533 A | 2/1997 | Stepniewski et al. | 424/78.02 |
| 5,623,017 A | 4/1997 | Hill | 524/860 |
| 5,833,965 A | * 11/1998 | Sun et al. | 424/66 |
| 5,919,437 A | 7/1999 | Lee et al. | 424/68 |
| 5,925,338 A | 7/1999 | Karassik et al. | 424/65 |
| 5,989,531 A | 11/1999 | Schamper et al. | 424/65 |
| 5,993,789 A | 11/1999 | Bonda et al. | 424/59 |
| 6,007,799 A | 12/1999 | Lee et al. | 424/65 |
| 6,060,546 A | 5/2000 | Powell et al. | 524/267 |

FOREIGN PATENT DOCUMENTS

| | | |
|---|---|---|
| EP | 0291334 | 11/1988 |
| EP | 0512770 | 11/1992 |
| WO | WO9219221 | 11/1992 |
| WO | WO9951192 | 10/1999 |

OTHER PUBLICATIONS

U.S. application No. 09/273,152, Potechin et al., filed Mar. 19, 1999.

* cited by examiner

Primary Examiner—Jose' G. Dees
Assistant Examiner—Konata M. George
(74) Attorney, Agent, or Firm—Rosemary M. Miano

(57) ABSTRACT

Low water emulsions are described which are useful for antiperspirants and/or deodorants wherein the emulsions are made by combining (I) 15–33% of an external phase comprising: (a) 1–25% of an organic ester having a refractive index in the range of 1.43–1.60 and capable of releasing an antiperspirant active to achieve a specified conductivity; (b) a sufficient amount of a silicone copolyol to achieve a solids content of 0.25–10%; (c) a sufficient amount of a volatile silicone to achieve a total amount of the external phase as 15–33%; (c) 0–5% of a silicone elastomer (on an actives basis); and (d) 0–15% of at least one emollient; and (II) 67–85% of an internal phase comprising: (a) an effective amount of at least one cosmetically active ingredient; (b) a sufficient amount of a solvent component to dissolve the cosmetically active ingredient with a maximum amount being about 80%; (c) 0.5–15 % of water optionally containing up to 30% of an ionizable salt soluble in water; (d) 0–5 % of a non-ionic emulsifier; and (e) 0–10% ethanol; wherein: (1) the final refractive index of the composition is in the range of 1.42–1.52; and (2) the conductance of the composition is at least 250 micro Siemens/cm/ml at a loading of at least 7% by weight level of antiperspirant active.

24 Claims, 1 Drawing Sheet

STABLE EMULSIONS FOR COSMETIC PRODUCTS

FIELD OF THE INVENTION

This invention relates to stabilized cosmetic products, especially antiperspirant and/or deodorant products which may include an antiperspirant active ingredient and a low water component which provides better efficacy and stability without compromising aesthetics. The compositions are emulsions made with an external (or oil) phase and an internal phase which contains the active ingredient. These emulsions may be used to form gel, soft solid or roll-on products.

BACKGROUND OF THE INVENTION

A large variety of antiperspirant and/or deodorant formulations have been described in the patent literature and/or have been made commercially available. These products have included suspension as well as emulsions. Also various physical forms may be used such as solids (for example, wax and gel sticks), semi-solids (for example, gels and creams), liquids (for example, roll-on products) and sprays (both aerosol and non-aerosol). In recent years a strong emphasis has been placed on improving both the performance and the aesthetics of these products. One of the particular problems is trying to obtain an emulsion product that has efficacy comparable to suspension products. A second problem is the stabilization of emulsion products to achieve a product that is shelf stable, but which releases an active ingredient in a timely manner.

With regard to emulsions, U.S. Pat. No. 4,673,570 to Soldati describes uniform, clear gelled antiperspirant compositions, free of waxes wherein the emulsions comprise in combination a volatile silicone fluid, a silicone emulsifier (such as a mixture of cyclomethicone and dimethicone copolyol), a destabilizing auxiliary emulsifier, water, a non-volatile emollient (such as C10–C20 alkyl fatty esters and ethers), linear silicone fluids, a coupling agent (such as low molecular weight alcohols and glycols), an active antiperspirant component and other ancillary agents.

U.S. Pat. No. 5,008,103 to Raleigh et al describes water-in-oil antiperspirant emulsions having a discontinuous polar phase containing water and optionally containing an emulsifier with a hydrophilic-lipophilic balance (HLB value) greater than 8, and a volatile silicone continuous phase with a dimethicone copolyol emulsifier. The HLB parameter is a well known parameter the calculation of which is disclosed and explained in numerous references. For nonionic surfactants, data obtained by actual analysis is usually a more accurate measure of HLB values (rather than theoretical determinations). For purposes of this invention it is intended that either the actual or theoretical HLB value may be used as the basis for selection. U.S. Pat. No. 5,401,870 to Raleigh et al and U.S. Pat. No. to 5,292,503 to Pereira et al describe similar subject matter.

U.S. Pat. No. 5,216,033 to Pereira et al describes a transparent water-in-oil emulsion containing a silicone phase with a dimethicone copolyol and an aqueous phase containing a refractive index "transparency structurant" to produce a refractive index matched clear emulsion. The transparency structurant is a C3–C8 polyhydric alcohol.

U.S. Pat. No. 5,599,533 to Stepniewski et al describes the use of silicone elastomer in an aqueous water-in-oil emulsion, but does not describe a clear emulsion.

U.S. Pat. No. 5,989,531 describes a liquid composition made with (a) an active phase comprising a selected glycol, a nonionic emulsifier having an HLB value greater than 8 and an antiperspirant and/or deodorant active; and (b) a silicone phase made with one or more of a dimethicone copolyols having an HLB less than 7 and nonionic emulsifiers having an HLB greater than 7, wherein the silicone phase has at least 10% silicone and the ratio of the silicone phase to he active phase is in the range of 1:1–1:4. Optional ingredients include the use of non-volatile silicones, volatile silicones and organic emollients.

U.S. Pat. No. 6,010,688 discloses the use of polyhydric alcohols to improve the stability and efficacy of antiperspirant formulations, particularly antiperspirant gels.

U.S. Pat. No. 5,955,065 discloses antiperspirant gel compositions containing soluble calcium salts. These compositions contain an aluminum or aluminum-zirconium antiperspirant salt and a water soluble calcium salt, both of which are suspended in a dermatologically acceptable anhydrous carrier vehicle. The present invention also embraces a method of inhibiting or reducing perspiration by topically applying an effective amount of such an antiperspirant composition to the skin.

U.S. Pat. No. 5,925,338 discloses a clear antiperspirant or deodorant gel composition which exhibits reduced staining while retaining excellent aesthetic attributes and efficacy. The oil phase comprises about 10 to 25% of the composition and contains a silicone oil and a polyether substituted silicone emulsifying agent. The silicone oil comprises a mixture of a non-volatile silicone, preferably a non-volatile linear silicone, and a volatile linear silicone. It has been found that reducing the amount of non-volatile silicone in the known gel composition to a relatively low level (e.g. below about 5%) and adding an amount of volatile linear silicone to the composition (e.g. above about 2%, preferably above about 5%) substantially improves the non-staining properties of the composition.

U.S. Pat. No. 5,623,017 discloses a clear silicone gel cosmetic composition with a water-containing internal phase. The silicone emulsifiers discussed are non-polymeric ethoxylated bis-trisiloxanes.

U.S. Pat. No. 6,007,799 discloses a clear cosmetic gel composition in the form of a water-in-oil emulsion, comprising (a) a water-based phase comprising water, a cosmetically active ingredient, and at least one coupling agent; and (b) an oil-based phase comprising a material having a refractive index in the range of 1.40–1.50, silicone fluids and an alkoxylated, alkyl substituted siloxane surface active agent (e.g., dimethicone copolyol). The composition has a refractive index in a range of 1.4026 to 1.4150. Where the cosmetically active ingredient is an antiperspirant active ingredient, the composition can be an antiperspirant gel (for example, soft gel) composition. In the refractive index range of the present invention, increased amounts of, for example, antiperspirant active ingredient, and other high-refractive-index materials providing cosmetic benefits, can be incorporated in the water and oil phases of the composition while still achieving a clear composition. The composition can also include polypropylene glycols (for example, tripropylene glycol), as part of the water-based phase, to provide a composition having reduced tackiness and reduced whitening (decreased residue); this composition is also mild.

U.S. Pat. No. 5,587,173 discloses a clear gel-type cosmetic product which has a viscosity of at least about 50,000 centipoise (cps) at 21° C., and includes an emulsion with an oil phase and a water phase that includes an incorporated active ingredient. The refractive indices of the water and oil phases match to at least 0.0004, the refractive index of the product is about 1.4000, and the product clarity is better than thirty NTU. These formulas contain 75–90% dispersed active phase. See also U.S. Pat. No. 4,021,536: which describes magnesium-zirconium complexes useful as antiperspirants; and U.S. Pat. No. 5,463,098 which describes clear antiperspirant gel stick and method for making same.

U.S. Pat. No. 3,979,510 describes aluminum-zirconium antiperspirant systems with complex aluminum buffers, including the use of various divalent metal ions in aluminum-zirconium antiperspirant formulations.

U.S. Pat. No. 4,980,156 discloses improved dry-feeling antiperspirant compositions which comprise an aqueous solution of an astringent emulsified in a volatile silicon fluid. The emulsion is stabilized by using a combination of a long-chain alkyl modified polysiloxane-polyoxyalkylene copolymer and an organic surfactant having an HLB value from 8 to 18.

U.S. Pat. No. 4,673,570 discloses uniform, clear gelled antiperspirant compositions, free of waxes and conventional gelling agents. The gel emulsions comprise, in combination, a volatile silicone fluid, a silicone emulsifier, a destabilizing auxiliary emulsifier, water, a non-volatile emollient, a coupling agent, an active antiperspirant component and ancillary agents.

U.S. Pat. No. 5,454,026 discloses a clear antiperspirant gel which is made by combining (a) an astringent compound having a refractive index of 1.48 to 1.53 which is an antiperspirant salt in the form of (i) a tray dried compound, (ii) an encapsulated salt, or (iii) a solvent solution of a salt compound; and (b) a clear anhydrous organic oil-free gel formed with 12-hydroxystearic acid as the gelling agent and a blend of aromatic containing silicone fluid and volatile silicone fluids.

U.S. Pat. No. 5,587,153 broadly discloses clear antiperspirant gels with a refractive index of 1.3975 to 1.4025 and a viscosity of 50,000–200,000 centipoise which are emulsions having 75–90% of a water phase.

U.S. Pat. No. 5,563,525 also discloses clear antiperspirant gels having a viscosity of at least 50,000 centipoise and a clarity better than 50 NTU which are emulsions having 75–90% of a water phase.

Historically, suspension products such as sticks have exhibited better efficacy than emulsion products. Previous attempts have not successfully overcome the problems of improving efficacy and achieving satisfactory formation of emulsions. Thus, it is an object of this invention to provide improved emulsions containing 0.5–15% water which exhibit improved efficacy which efficacy is comparable to that achieved in suspension products and, at the same time, have a stability profile that allows for satisfactory stability on the shelf. Another issue is the formation of emulsions which are stable on the shelf but which destabilize sufficiently after application to a skin surface so as to release an efficacious amount of an active ingredient. Thus, it is an object of the present invention to provide emulsions with those characteristics. It is also an object of this invention to provide gel or soft solid compositions which can, if desired, be formed into clear compositions. It is still another object of this invention to provide compositions that can, if desired, be formed into clear compositions without the use of microemulsions.

SUMMARY OF THE INVENTION

This invention relates to a low water, cosmetic composition comprising (a) 15–33% of an external phase (also called the oil phase) which is made with at least one high refractive index (RI in the range of 1.43–1.60) organic ester as described below; a volatile silicone based emulsifier; and a volatile silicone; and (b) 67–85% of an internal phase which is made with 0.5–15%, particularly a minimum of 2% water or salt water; and at least one active ingredient selected from the group consisting of antiperspirant actives (particularly in a glycol solvent), antimicrobials and fragrances, wherein (a) the refractive index of the final cosmetic composition is in the range of 1.42–1.52 and, in a particular embodiment, (b) the conductance of a water droplet applied to the surface of a thin film of the cosmetic composition is at least 250 micro Siemens/cm/ml as measured by the fixed geometry test described below at a loading of at least 7% by weight level of antiperspirant active as measured by a specified test described below, with more particular embodiments having conductances greater than 300 micro Siemens/cm/ml, particularly greater than 400 micro Siemens/cm/ml and especially greater than 500 micro Siemens/cm/ml.

It is important to note that while traditional gels contain on the order of 33–50% water, the emulsions of this composition contain 0.5–15% water.

Figure 1:
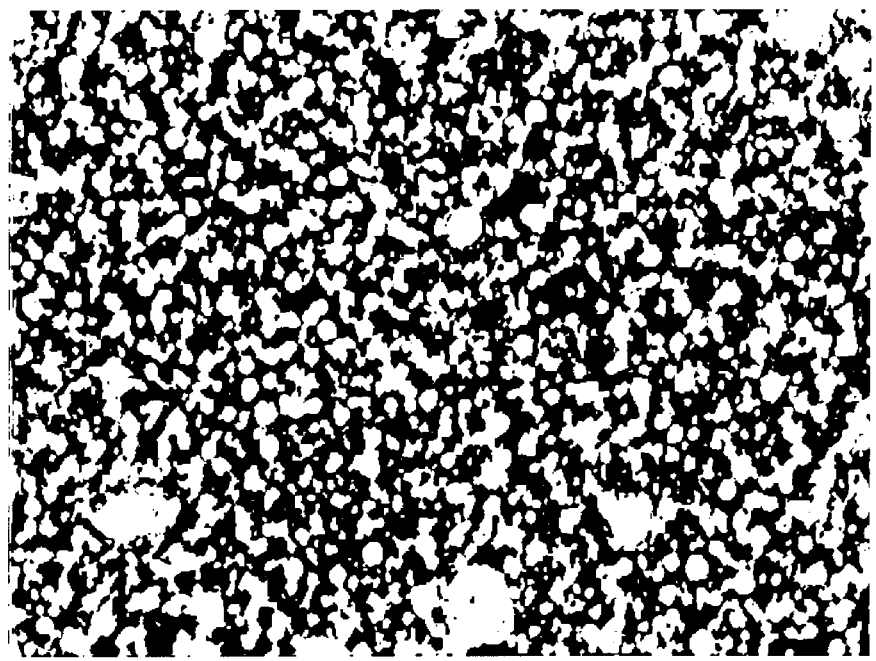
FIG. 1 is a graphical representation of a photomicrograph as may be obtained from an optical microscope with contrast enhanced optics at a magnification power of 400× for an emulsion of the invention as it would appear prior to application.
Figure 2:
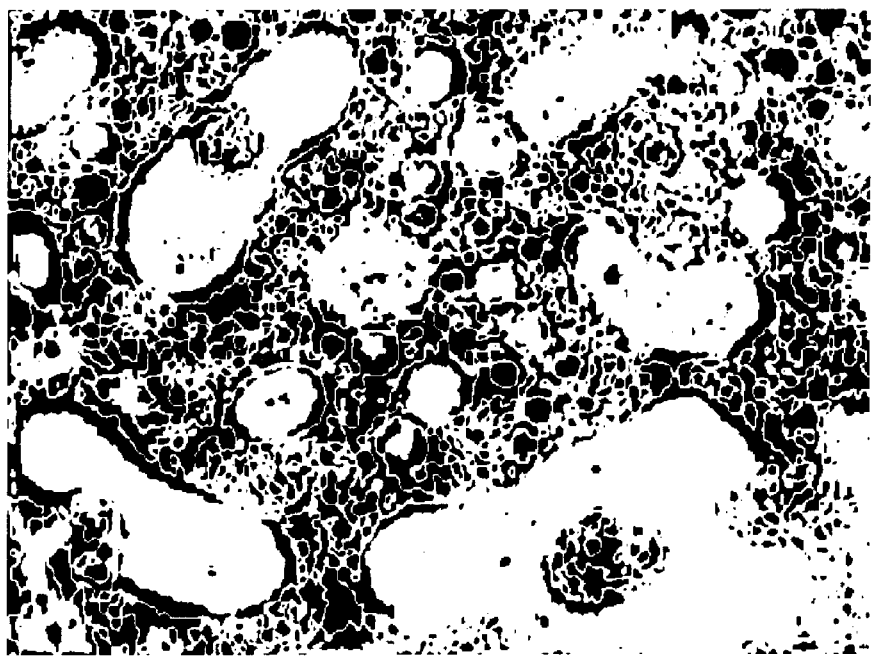
FIG. 2 is a graphical representation of a photomicrograph as may be obtained from an optical microscope with contrast enhanced optics at a magnification power of 400× for an emulsion of the invention after 30 minutes on a skin surface.

A comparison between FIGS. 1 and 2 shows that the emulsion is stable in the product container and then breaks down in use on skin to release the active ingredient. The shaded areas represent the external phase.

An emulsion that is representative of the type used for generating the FIGS. 1 and 2 is described in Example 3.

DETAILED DESCRIPTION OF THE INVENTION

The low water emulsions of this invention are made by combining 15–33% of an external phase and 67–85% of an internal phase as described below:
External Phase (also referred to as the continuous phase) comprising:
  (a) 1–25% of an organic ester having a refractive index in the range of 1.43–1.60 and which allows the release of an antiperspirant active especially as marked by a specified minimum conductance;
  (b) a sufficient amount of a silicone copolyol to achieve a solids content of 0.25–10% (particularly 0.9–4.0% and, more particularly, 1.0–3.0%) wherein the silicone copolyol may be added with or without solvent;
  (c) a sufficient amount of a volatile silicone (for example, a cyclomethicone such as a D5 cyclomethicone) to achieve a quantum sufficient ("q.s.") amount of the external phase as 15–33% (for example, wherein part of the volatile silicone may be added in a silicone copolyol which itself is obtained already mixed with a volatile silicone as a solvent, such as a 40–48% dimethicone copolyol in cyclomethicone) (more particularly, 35–55% of a glycol component for an antiperspirant product and 50–80% of a glycol component for a deodorant product);

(d) 0–5% of a silicone elastomer (on an actives basis); and
(e) 0–15%, particularly 0–10% and, more particularly, 0–5% of at least one emollient;

Internal Phase (also referred to as the dispersed phase) comprising:
  (a) an effective amount of at least one cosmetically active ingredient selected from the group consisting of 0.1–25% of an antiperspirant active (on an anhydrous basis), 0.1–3% of a fragrance, and 0.05–5% of an antimicrobial;
  (b) a sufficient amount of a solvent component to dissolve the cosmetically active ingredient and to complete the internal phase (for example, a glycol component to dissolve an antiperspirant active), with a maximum amount being about 70% of solvent for a deodorant product and abut 80% for an antiperspirant product;
  (c) 0.5–15% of water optionally containing up to 30% of an ionizable salt soluble in water (for example, NaCl, KCl, $ZnCl_2$, zinc citrate and zinc glycinate);
  (d) 0–5% of a non-ionic emulsifier; and
  (e) 0–10% ethanol; wherein:
    (1) the final refractive index of the composition is in the range of 1.42–1.52 (particularly 1.43–1.45); and
    (2) all amounts are in percent by weight based on the entire weight of the composition.

In a particular embodiment, the conductance of a water droplet applied to the surface of a thin film of the cosmetic composition is at least 250 micro Siemens/cm/ml at a loading of at least 7% by weight level of antiperspirant active as measured by the fixed geometry test described below with more particular embodiments having conductances greater than 300 micro Siemens/cm/ml, particularly greater than 400 micro Siemens/cm/ml and especially greater than 500 micro Siemens/cm/ml.

The organic esters useful in this invention include, those of formula R"—CO(O)—R', where each of R' and R" is independently selected from the group consisting of (a) C1–C30-straight and branched chain alkyls and alkenyls; and (b) an aromatic group such as phenyl, benzyl, naphthyl, or biphenyl wherein the aromatic is optionally substituted by one or more or the groups listed in (a), but provided that the total of the carbons for R'+R" is in the range of 8–30.

Examples of suitable esters include, for example, C12–15 alkyl benzoate (such as FINSOLV TN from Finetex, Elmwood Park, N.J.); octyl methoxy cinnamate (such as ESCALOL 557 from ISP, Wayne, N.J. (but in amounts less than 6% because of irritancy); isostearyl isostearate (such as (PRISORINE IS 2039 from Unichema, Chicago, Ill.); benzyl benzoate; 2,6-di-(ethylhexyl)naphthalate (such as Hallbrite TQ from the C.P. Hall Company, Bedford Park, Ill.); butyl octyl salicylate; glyceryl monostearate; n-dibutyl sebacate; isopropyl myristate; isopropyl palmitate; butyl stearate; cetyl lactate; isocetyl stearate; hexyl laurate; decyl oleate; isostearyl isostearate; ethyl hexyl maleate; sorbitan monoaurate; sorbitan monooleate; sorbitan sesquioleate; sorbitan trioleate; isopropyl palmitate; isopropyl stearate; stearyl stearate; diisopropyl adipate; diisopropyl sebacate; butyl myristate; and isopropyl laurate.

Particular esters of interest are 2,6-di-(ethylhexyl) naphthalate, octyl methoxy cinnamate; isostearyl stearate; and C12–15 alkyl benzoate.

In general, silicone copolyols useful in the present invention include copolyols of the following Formulae I and II. Formula I materials may be represented by:

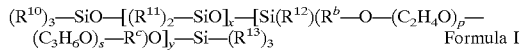
Formula I wherein each of $R^{10}$, $R^{11}$, $R^{12}$ and $R^{13}$ may be the same or different and each is selected from the group consisting of C1–C6 alkyl; $R^b$ is the radical —$C_mH_{2m}$—; $R^c$ is a terminating radical which can be hydrogen, an alkyl group of one to six carbon atoms, an ester group such as acyl, or an aryl group such as phenyl; m has a value of two to eight; p and s have values such that the oxyalkylene segment —$(C_2H_4O)_p$—$(C_3H_6O)_s$— has a molecular weight in the range of 200 to 5,000; the segment preferably having fifty to one hundred mole percent of oxyethylene units —$(C_2H_4O)_p$— and one to fifty mole percent of oxypropylene units —$(C_3H_6O)_s$—; x has a value of 8 to 400; and y has a value of 2 to 40. Preferably each of $R^{10}$, $R^{11}$, $R^{12}$ and $R^{13}$ is a methyl group; $R^c$ is H; m is preferably three or four whereby the group $R^b$ is most preferably the radical —$(CH_2)_3$—; and the values of p and s are such as to provide a molecular weight of the oxyalkylene segment —$(C_2H_4O)_p$—$(C_3H_6O)_s$— of between about 1,000 to 3,000. Most preferably p and s should each have a value of about 18 to 28.

A second siloxane polyether (copolyol) has the Formula II:

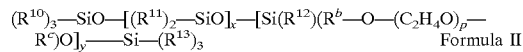
Formula II wherein p has a value of 6 to 16; x has a value of 6 to 100; and y has a value of 1 to 20 and the other moieties have the same definition as defined in Formula I.

It should be understood that in both Formulas I and II shown above, that the siloxane-oxyalkylene copolymers of the present invention may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Thus, one or more of the $R^{10}$, $R^{11}$, $R^{12}$ and $R^{13}$ substituents which are attached to the two terminal silicon atoms at the end of the siloxane chain can be substituted with the segment —$R^b$—O—$(C_2H_4O)_p$—$(C_3H_6O)_s$—$R^c$ or with the segment —$R^b$—O—$(C_2H_4O)_p$—$R^c$. In some instances, it may be desirable to provide the segment —$R^b$—O—$(C_2H_4O)_p$—$(C_3H_6O)_s$—$R^c$ or the segment —$R^b$—O—$(C_2H_4O)_p$—$R^c$ at locations which are in the siloxane chain as well as at locations at one or both of the siloxane chain ends.

Particular examples of suitable dimethicone copolyols are available either commercially or experimentally from a variety of suppliers including Dow Corning Corporation, Midland, Mich.; General Electric Company, Waterford, N.Y.; Witco Corp., Greenwich, Conn.; and Goldschmidt Chemical Corporation, Hopewell, Va. Examples of specific products include DOW CORNING® 5225C from Dow Corning which is a 10% dimethicone copolyol in cyclomethicone; DOW CORNING® 2-5185C which is a 45–49% dimethicone copolyol in cyclomethicone; SIL WET L-7622 from Witco; ABIL EM97 from Goldschmidt which is a 85% dimethicone copolyol in D5 cyclomethicone; and various dimethicone copolyols available either commercially or in the literature.

It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone. The higher concentration materials such as DOW CORNING® 2-5185 material is of particular interest.

In one particular embodiment 0.1–40% (particularly 10–40%) of a 10–50% silicone copolyol such as dimethicone copolyol in cyclomethicone mixture may be used, wherein the amount of mixture added is selected so that the level of silicone copolyol in the cosmetic composition is in the range of 1.0–3.0% (particularly 2%) (for example, 0.25–10% of a 40%–45% dimethicone copolyol in cyclomethicone mixture).

By volatile silicone material is meant a material that has a measurable vapor pressure at ambient temperature. For the volatile silicone portion, examples of volatile silicones (particularly silicones with a boiling point of 250 degrees C or less at atmospheric pressure) include cyclomethicone (especially cyclopentasiloxane, also called "D5"), "hexamethyldisiloxane", and low viscosity dimethicone (for example, Dow Corning® 200 fluid having a viscosity of 1–200 centistokes). Such volatile silicones include conventional cyclic and linear volatile silicones Illustratively, and not by way of limitation, the volatile silicones are one or more members selected from the group consisting of cyclic polydimethylsiloxanes such as those represented by Formula III:

Formula III

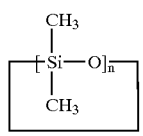

where n is an integer with a value of 3–7, particularly 5–6. For example, DC-245 fluid (or the DC-345 version) from Dow Corning Corporation (Midland, Mich.) is a type of cyclomethicone which can be used. These include a tetramer (or octylmethylcyclotetrasiloxane) and a pentamer (or decamethylcyclopentasiloxane). The volatile linear silicones can also be included in this group of volatile silicones and are one or more members selected from the group consisting of linear polydimethylsiloxanes such as those represented by Formula IV:

Formula IV

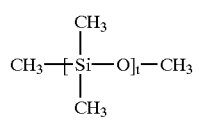

and t is selected to obtain a viscosity of 1–200 centistokes.

It is also possible to include a silicone elastomer in the external phase. The elastomer may also be added in a carrier such as cyclomethicone. Suitable elastomers include those described in, for example, U.S. Pat. No. 6,060,546 assigned to General Electric Company; and copending PCT case WO 99/51192, both of which are incorporated by reference herein for the description of the elastomers. Particular examples of suitable elastomers are SFE 167, a cetearyl dimethicone/vinyl dimethicone crosspolymer from GE Silicones (Waterford, N.Y.); SFE168, a cyclomethicone (and) dimethicone/vinyl dimethicone crosspolymer from GE Silicones; vinyl dimethicone crosspolymers such as those available from Shin Etsu Silicones of America (Akron, Ohio) under trade names KSG-15 (cyclomethicone (and) dimethicone/vinyl dimethicone crosspolymer), KSG-16 (dimethicone (and) dimethicone/vinyl dimethicone crosspolymer), KSG-17 (cyclomethicone (and) dimethicone/vinyl dimethicone crosspolymer), KSG-18 (phenyl trimethicone (and) dimethicone/phenyl vinyl dimethicone crosspolymer); and KSG-20 (dimethicone copolyol crosspolymer; dimethicone/vinyl dimethicone crosspolymer from Dow Corning Corporation (Midland, Mich.) under trade name Dow Corning 9506 Cosmetic Powder; and a mixture of cyclomethicone and stearyl-vinyl/hydromethylsiloxane copolymer available from Grant Industries, Inc. (Elmwood Park, N.J.) under the trade name Gransil SR-CYC.

For the antiperspirant active used in the internal (also called "active") phase various antiperspirant active materials that can be utilized according to the present invention provided that they are soluble at a suitable concentration in the active phase. These include conventional aluminum and aluminum/zirconium salts, as well as aluminum/zirconium salts complexed with a neutral amino acid such as glycine, as known in the art. See each of European Patent Application Number. 512,770 A1 and PCT case WO 92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention if they are soluble in the active phase. Suitable materials include (but are not limited to) aluminum chlorides (various types including, for example, anhydrous form, hydrated form, etc.), zirconyl hydroxychlorides, zirconyl oxychlorides, basic aluminum chlorides, basic aluminum chlorides combined with zirconyl oxychlorides and hydroxychlorides, and organic complexes of each of basic aluminum chlorides with or without zirconyl oxychlorides and hydroxychlorides and mixtures of any of the foregoing. These include, by way of example (and not of a limiting nature), aluminum chlorohydrate, aluminum chloride, aluminum sesquichlorohydrate, aluminum chlorohydrol-propylene glycol complex, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum dichlorohydrate, aluminum chlorohydrex PG, aluminum chlorohydrex PEG, aluminum dichlorohydrex PG, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as tin or titanium salts used alone or in combination with aluminum compounds (for example, aluminum-stannous chlorohydrates), aluminum nitratohydrate and its combination with zirconyl hydroxychlorides and nitrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy aluminum/zirconium salt-glycine materials, having enhanced efficacy due to improved molecular distribution, known in the art and discussed, for example, in PCT No. WO92/19221, the contents of which are incorporated by reference in their entirety herein. Particular actives include Westchlor A2Z 4105 aluminum zirconium tetrachlorohydrex gly propylene glycol complex, (from Westwood Chemical Corporation, Middletown, N.Y.); Westchlor ZR 35B aluminum zirconium tetrachlorhydrex gly, and Rezal 36 GP and AZP 902 aluminum zirconium tetrachlorhydrex gly both from Reheis, Berkeley Heights, N.J.

Antiperspirant actives can be incorporated into compositions according to the present invention in amounts in the range of 0.05–25% (on an anhydrous solids basis), preferably 5–25%, by weight, of the total weight of the composition. The amount used will depend on the formulation of the composition. For example, at amounts in the lower end of the broader range (for example, 0.05–5%), the antiperspirant active material will not substantially reduce the flow of perspiration, but will reduce malodor, for example, by acting as a deodorant material. At amounts at the higher end of the range (especially using a minimum of 7% and, more particularly, in a range of 9–20%, an antiperspirant effect can be expected.

Deodorant active materials can be selected from several types of materials:

(a) lesser amounts of antiperspirant actives, such as in the range of 0.1–5.0 percent by weight based on the total weight of the composition;

(b) fragrances, such as in the range of 0.5–3.0 percent by weight based on the total weight of the composition;

(c) effective amounts of antimicrobial agents, for example, 0.05–5.0 percent (particularly 0.1–1% and, more particularly, 0.25–1.0%) by weight based on the total weight of the composition; examples include bacteriostatic quaternary ammonium compounds (such as cetyl trimethyl-ammonium bromide, and cetyl pyridinium chloride), 2,4,4'-trichloro-2'-hydroxydiphenylether (Triclosan), N-(4-chlorophenyl)-N'-(3,4-dichlorophenyl)urea (Triclocarban), silver halides, octoxyglycerin (SENSIVA™ SC 50) and various zinc salts (for example, zinc ricinoleate). Triclosan or Triclocarban can, illustratively, be included in an amount of from 0.05% to about 0.5% by weight, of the total weight of the composition.

The glycol or polyglycol is selected from the group consisting of ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof. More particular examples of the glycol component include one or more members of the group consisting of propylene glycol, dipropylene glycol, tripropylene glycol, 2-methyl-1,3-propanediol, methyl propylene glycol, low molecular weight (less than 600) polyethylene glycol, low molecular weight (less than 600) polypropylene glycols, and mixtures of any of the foregoing. Propylene glycol is of particular interest because the antiperspirant active is more soluble in this type of glycol. Tripropylene glycol has lower irritancy, but the antiperspirant active is not as soluble in this glycol. Mixtures of glycols may be used to balance these desirable properties.

One of the important aspects of the invention is the presence of water in an amount of 0.5–15% (particularly 2–15%) which optionally contains up to 30% of an ionizable salt of the form $M_aX_b$ where a=1 or 2; b=1 or 2; M is a member selected from the group consisting of $Na^{+1}$, $Li^{+1}$, $K^{+1}$, $Mg^{+2}$, $Ca^{+2}$, $Sr^{+2}$, $Sn^{+2}$, and $Zn^{+2}$; member selected from the group consisting of chloride, bromide, iodide, citrate, gluconate, lactate, glycinate, glutamate, ascorbate, aspartate, nitrate, phosphate, hydrogenphosphate, dihydrogenphosphate, formate, malonate, maleate, succinate, carbonate, bicarbonate, sulfate and hydrogensulfate. A salt of particular utility is NaCl. As will be appreciated by those skilled in the art, while it may be possible under certain circumstances to add a salt directly to a portion of the mixture during manufacturing, it is preferred to add the salt as a mixture or solution of the salt in a carrier or solvent, particularly water. Of course, various concentration of the salt can be made such as in the range of 1–40%, particularly 10–30% and, more particularly, 25–30%.

It has been found that the use of water or salt water stabilizes the emulsion which would otherwise not last more than about 7 days at 49 degrees C. However, the amount of water used here does not result in compositions which are so stable that they do not release the active ingredient when the compositions are applied to the skin. The low amount of water used in these compositions is also important as it decreases the degradation of the active, especially an antiperspirant salt, which is susceptible to polymerization with a decrease in efficacy.

The stability of the emulsions of the invention may be measured by (1) visually evaluating the emulsions for phase separation and (2) for gels, further monitoring the rheology using the viscosity tests described below.

The compositions of the present invention can include other optional ingredients to improve the aesthetics and/or performance of the cosmetic compositions of the invention. These include colorants, fillers, fragrances, emollients, masking agents, water soluble emollients, hydrogen bonding modifiers (for example, urea, guanidine hydrochloride, xylitol, trehalose, maltose and glycerine), additional fragrances, additional preservatives, etc. Such one or more other optional ingredients can be added to the internal or external phases or both in appropriate amounts. For example, fragrances will frequently be partitioned to both the external and internal phases regardless of when or to what phase (or final product) the fragrance is added.

In a preferred embodiment the refractive indices of the external and internal phases are matched within 0.01 to obtain a clear product.

Emollients are a known class of materials in this art, imparting a soothing effect to the skin. These are ingredients which help to maintain the soft, smooth, and pliable appearance of the skin. Emollients are also known to reduce whitening on the skin and/or improve aesthetics. Examples of chemical classes from which suitable emollients can be found include:

(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula VI:

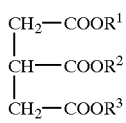

Formula VI wherein each of $R^1$, $R^2$, and $R^3$ may be the same or different and have a carbon chain length (saturated or unsaturated) of 7 to 30. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil.

(b) hydrocarbons which are a group of compounds containing only carbon and hydrogen. These are derived from petrochemicals. Their structures can vary widely and include aliphatic, alicyclic and aromatic compounds. Specific examples include paraffin, petrolatum, hydrogenated polyisobutene, and mineral oil.

(c) saturated and unsaturated fatty alcohols (primary, secondary and tertiary alcohols, and including guerbet alcohols) with general structure:

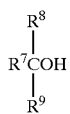

wherein each of $R^7$, $R^8$ and $R^9$ is hydrogen or a straight or branched chain carbon group and the total number of carbons in $R^7+R^8+R^9$ is in the range of 7–30. Specific examples include lauryl, myristyl, cetyl, isocetyl, stearyl, isostearyl, oleyl, ricinoleyl and erucyl alcohol.

(d) lanolin and its derivatives which are a complex esterified mixture of high molecular weight esters of (hydroxylated) fatty acids with aliphatic and alicyclic alcohols and sterols as well as propoxylated and/or butoxylated species. Specific examples include lanolin, lanolin oil, lanolin wax, lanolin alcohols, lanolin fatty acids, isopropyl lanolate, propoxylated lanolin, butoxylated lanolin, and acetylated lanolin alcohols.

(e) alkoxylated alcohols wherein the alcohol portion is selected from aliphatic alcohols having 2–18 and more particularly 4–18 carbons, and the alkylene oxide portion is selected from the group consisting of propylene oxide and butylene oxide having a number of alkylene oxide units from 2–53 and, more particularly, from 2–15. Specific examples include PPG-14 butyl ether and PPG-53 butyl ether.

(f) miscellaneous which are selected from the group consisting of neopentyl glycol diheptanoate, PEG-8 laurate, isocetyl stearate, dimethicone copolyol laurate, Dow Corning 2501 cosmetic wax (dimethicone copolyol); isostearyl isostearate, isostearyl palmitate, isostearyl alcohol, PPG-5-ceteth-20, PPG-10-cetyl ether, triethyl hexanoin, ethyl hexyl isostearate, glyceryl oleate, and isopropyl isostearate.

(g) mixtures and blends of two or more of the foregoing.

Particular examples of suitable emollients include members of the group consisting of Octyloxyglyderin (SENSIVA SC50 from Schuilke Mayr, Norderstedt, Germany) (which can be used as an emollient as well as an antibacterial); Polysorbate 80 (TWEEN 80 from ICI Americas, Wilmington, Del.); Oleth-20; ethoxylated alcohols such as steareth-2, nonoxynol-2, PPG-4-Ceteth-1; ethoxylated carboxylic acids such as PEG-4 dilaurate, PEG-2 oleate; glyceryl esters such as PEG-2 castor oil, polyglyceryl-3 oleate, glyceryl stearate; sorbitan derivatives such as sorbitan oleate; PPG-3 myristyl ether (such as WITCONOL APM from Goldschmidt), a dimethiconol (such as Dow Corning® DC1501 dimethiconol), neopentyl glycol diheptanoate, PEG-8 laurate, isocetyl stearate, dimethicone copolyol laurate, Dow Corning 2501 cosmetic wax (dimethicone copolyol); isostearyl isostearate, isostearyl palmitate, isostearyl alcohol, PPG-5-ceteth-20, PPG-10-cetyl ether, triethyl hexanoin, ethyl hexyl isostearate, glyceryl oleate, and isopropyl isostearate.

The release of antiperspirant actives into the sweat is a significant event in the development of an antiperspirant effect. The magnitude of the antiperspirant effect is related to the concentration of the antiperspirant salt in the sweat, and therefore measuring the concentration of antiperspirant salt can provide an estimate of antiperspirant efficacy. A variety of methods can be used to evaluate antiperspirant salt concentration, ranging from atomic absorption, ICP, and HPLC to solution conductance of aqueous films. The later method is especially well suited for measuring the release of small amounts of antiperspirant salts. The methods outlined below use solution conductance to estimate antiperspirant salt release upon short exposures to deionized water.

As noted above, the conductance of the compositions of the invention is defined with reference to a value of at least 250 micro Siemens/cm/ml when the composition is loaded with at least 7% of an antiperspirant active (such as the antiperspirant actives listed above) and when the conductance is measured by a fixed geometry test. For purposes of clarification is should be explained that there are a variety of tests and test conditions that can be used to evaluate:

(1) "Conductance" is defined as an absolute measure of current flow through a solution with the dimensions of micro Siemens/cm, which value is independent of probe geometry. This value is divided by the volume (in ml) of applied water to give the conductance number with the units of micro Siemens/cm/ml. This test is deemed a more reproducible measurement since it references a set of fixed dimensions and units.

(2) Alternatively, "conductivity" as a measure of current flow through a solution without reference to probe geometry, and which is measured in micro Siemens. This test is convenient for quick screening of solutions.

Standard Test for Thin Film Conductivity

One test for conductivity is called herein the "standard" test. A non-conducting plastic block (for example, made from PLEXIGLAS® material) to form an oral shaped well 12.2 cm×2.5 cm with a depth of 100 microns. This depth corresponds to the mean thickness of an antiperspirant product applied to the underarm of a human person during real use conditions (approximately 50 to 100 microns). An aliquot of test sample is placed in the well of the block sufficient to fill the well to the brim. Excess sample is scraped off by running a flat edged instrument over the surface of the block. The sample block, with the product film, is then either (a) equilibrated at room temperature for two hours or (b) placed in a synthetic underarm to simulate in vivo conditions. If method (b) is used, the air temperature inside the synthetic underarm is maintained at 33 to 35° C. and a relative humidity of 85 to 95%, and the sample blocks are placed on a temperature controlled surface maintained at body temperature (37° C.). These conditions closely approximate the temperature gradients normally found in the underarm. Samples are equilibrated in either the (a) or (b) environments for two hours prior to measurement of antiperspirant salt release by solution conductivity. After two hours the sample blocks are removed from the controlled environment and placed on a stage for conductivity measurement. An aliquot of 250 microliters of water with a resistance of at least 17 mega ohms is placed on the surface of the sample film, and the conductance of the water is measured as a function of time with a Skicon 200 Skin surface Hygrometer (I.B.S. Co., Ltd., Shizuoka-ken, 430, Japan) using an Elsnau (MT-8C Probe) electrode (Todd Maibach & Associates, San Francisco, Calif.). The electrode is positioned so that it touches the bottom of the test sample in the well. Conductivity is measured in micro Siemens at 3.5 MHz. Data is collected at 0.1 sec intervals for approximately 100 sec. Solution conductivity after 10 seconds of exposure to the water is used to compare the release of active salt for different formulations This method is believed to be particularly useful for evaluating the release of antiperspirant salts in the absence of other salts. The standard method is useful as a quick screening tool for active salt release studies. A solution conductivity of approximately 400 or greater micro Siemens at 10 sec after application of the water droplet to the surface of the test sample, can be considered evidence of significant release of the antiperspirant active salt from the film surface and correlates with improved antiperspirant efficacy.

Fixed Geometry Test for Thin Film Conductance

One of the limitations of the Standard Test is that the area of the water droplet is not controlled and, therefore, the apparent conductance (which is measured as conductivity because the water volume is not controlled) is dependent on droplet spreading. This will lead to an underestimate of the actual solution conductance (and therefore antiperspirant salt release), of water drops which spread significantly. In order to measure the absolute concentration of the antiperspirant salts the spreading of the water drop must be stopped. This can be accomplished by placing a well of know dimensions on the surface of the product film to establish an area of constant size that is exposed to the water droplet. A more predictable test is needed, such as the Fixed Geometry Test.

The Fixed Geometry Test uses the same basic technique as the Standard Test in terms of preparation of the test well, addition of the test sample and equilibration of the sample to a selected temperature. Instead of allowing the water to flow freely on the surface of the test film, however, a second structure of non-conducing plastic predrilled with holes of a fixed diameter is clamped over the well block. The second structure with holes is also made of a non-conducting material (such as PLEXIGLAS material), is open on both ends and has an internal diameter of 1.905 cm. The bottom of each predrilled hole is fitted with a small O-ring to prevent leakage of the water. A 400 microliter aliquot of water (rather than the 250 microliter aliquot used in the Standard Test) with a resistance of 17 mega Ohms is then placed in the hole to cover the test sample. This will normally result in a liquid height for water of about 1.4 mm. The Elsnau probe is positioned through the drilled hole so that the bottom of the probe rests on the bottom of the well at a right angle. Because of the fixed shape, data can be obtained as conductance in micro Siemens/cm/ml using the method described for calculation.

As will be appreciated by those skilled in the art, a variety of other shapes, sizes and orientations of electrodes can be used. In another variation on the Fixed Geometry Test, thin gold wires (99% purity, set of 2, each about 1 mm in diameter) can be constructed to be in parallel with the surface of the water (and covered by the water) and conductance can be measured.

The electrode used in both types of tests must be calibrated so that a conductivity in micro Siemens can be obtained. Such calibration with a salt solutions in water of known conductance is known to those skilled in the art.

While different readings can be obtained depending on the thickness of the films, the test used, etc. it is important to establish a standard test for purposes of defining conductivity according to this invention. The Fixed Geometry Test is set as the defining test because it is believed to be more reproducible. Thus a minimum conductance value of 250 micro Siemens/cm/ml is the lower limit. Interestingly, minimum values for the Standard Test seemed to run about 400 micro Siemens due to the way the test was conducted. For the data described here, samples should be placed in a chamber at the humidity and elevated temperature conditions described above for about 2 hours. Samples not subjected to elevated temperatures should give higher values.

An average efficacy gel having a water content of greater than 35%(such as Gillette's Right Guard Antiperspirant Gel) was compared with an improved gel made according to Example 3, below. The average efficacy gel has a standard conductivity of 295±35micro Siemens at 10 seconds and a fixed geometry conductivity of 121±47 micro Siemens/cm/ml at 10 seconds. The improved formulation made according to this invention had a standard conductivity of 1884±225 micro Siemens at 10 seconds and a fixed geometry conductance of 1213±43 micro Siemens/cm/ml at 10 seconds. The improved formulation was ranked as above average in efficacy in a clinical test whereas the average gel was ranked as average in efficacy in a clinical test.

While it is not known precisely how the compositions of this invention work, it has been observed that they have a combination of two important properties. These compositions exhibit superior stability on the shelf and yet degrade on contact with the skin to release the active ingredient with a higher level of efficacy than is usually achieved. The deodorant and/or antiperspirant compositions disclosed in this invention form metastable emulsions when deposited on the skin. The decomposition of these emulsions upon application can be assessed by the thin film conductance method described herein. In another test the superiority of this invention is evaluated by applying test sample on skin, waiting 30 minutes, gently scraping the sample off the skin, placing the scraped emulsion on a slide with a cover and examining the product film under a microscope with contrast enhanced optics. Comparison to another experimental low efficacy formulations containing an antiperspirant active shows that the emulsions of effective formulations break up on the skin while the emulsions of the low efficacy samples remain intact. (See FIGS. 1 and 2 above.)

Particular formulations of interest include:

Formulation A:

External Phase comprising:
      (a) 0.5–25% (particularly 5–15%) of C12–15 alkyl benzoate;
      (b) 0.1–7% (particularly 2–5%) of a 40% dimethicone copolyol in cyclomethicone);
      (c) 0–25% (particularly 5–15%) of a volatile silicone (for example, a cyclomethicone such as a D5 cyclomethicone);
      (d) 0–5% (particularly 0.1–2%) of a silicone elastomer (actives basis) (cyclomethicone carrier);

Internal Phase comprising:
      (a) 0.1–25% of an antiperspirant active (on an anhydrous basis) (especially 7–25% for an antiperspirant or 0.1–5% for a deodorant);

(b) a sufficient amount of a glycol component such as propylene glycol to dissolve the antiperspirant active and to complete the internal phase;
(c) 0.5–15% (particularly 2–5%) water;
(d) 0–5% nonionic emulsifier (for example, Oleth-20);
(e) 0–3% NaCl (0–3% on a dry basis but added in a 20–30% water solution).

Formulation B:
External Phase comprising:
(a) 0.5–25% of octyl methoxy cinnamate;
(b) 0.1–7% (particularly 2–5%) of a 40% dimethicone copolyol in cyclomethicone);
(c) 0–25% (particularly 5–15%) of a volatile silicone, (for example, a cyclomethicone such as a D5 cyclomethicone);
(d) 0–5% (particularly 0.1–2%) of a silicone elastomer (actives basis) (cyclomethicone carrier);
Internal Phase comprising:
(a) 0.1–25% of an antiperspirant active (on an anhydrous basis) (especially 7–25% for an antiperspirant or 0.1–5% for a deodorant);
(b) a sufficient amount of a glycol component such as propylene glycol to dissolve the antiperspirant active and to complete the internal phase;
(c) 0.5–15% (particularly 2–15%) water;
(d) 0–5% nonionic emulsifier (for example, Oleth-20);
(e) 0–3% NaCl (0–3% on a dry basis but added in a 20–30% water solution).

Formulation C:
External Phase comprising:
(a) 0.5–25% of isostearyl isostearate;
(b) 0.1–7% (particularly 2–5%) of a 40% dimethicone copolyol in cyclomethicone);
(c) 0–25% (particularly 5–15%) of a volatile silicone, (for example, a cyclomethicone such as a D5 cyclomethicone);
(d) 0–5% (particularly 0.1–2%) of a silicone elastomer (actives basis) (cyclomethicone carrier);
Internal Phase comprising:
(a) 0.1–25% of an antiperspirant active (on an anhydrous basis) (especially 7–25% for an antiperspirant or 0.1–5% for a deodorant);
(b) a sufficient amount of a glycol component such as propylene glycol to dissolve the antiperspirant active and to complete the internal phase;
(c) 0.5–15% (particularly 2–15%) water;
(d) 0–5% nonionic emulsifier (for example, Oleth-20);
(e) 0–3% NaCl (0–3% on a dry basis but added in a 20–30% water solution).

Formulation D:
External Phase comprising:
(a) 0.5–25% of benzyl benzoate;
(b) 0.1–7% (particularly 2–5%) of a 40% dimethicone copolyol in cyclomethicone);
(c) 0–25% (particularly 5–15%) of a volatile silicone, (for example, a cyclomethicone such as a D5 cyclomethicone);
(d) 0–5% (particularly 0.1–2%) of a silicone elastomer (actives basis) (cyclomethicone carrier);
Internal Phase comprising:
(a) 0.1–25% of an antiperspirant active (on an anhydrous basis) (especially 7–25% for an antiperspirant or 0.1–5% for a deodorant);
(b) a sufficient amount of a glycol component such as propylene glycol to dissolve the antiperspirant active and to complete the internal phase;
(c) 0.5–15% (particularly 2–15%) water;
(d) 0–5% nonionic emulsifier (for example, Oleth-20);
(e) 0–3% NaCl (0–3% on a dry basis but added in a 20–30% water solution).

Formulation E:
External Phase comprising:
(a) 0.5–25% (particularly 1–10% of a combination of 2,6 diethylhexylnaphthalate, isostearyl stearate and C12–15 alkyl benzoate wherein the mixture of esters has a refractive index in the range of 1.45–1.54;
(b) 0.1–7% (particularly 2–5%) of a 40% dimethicone copolyol in cyclomethicone);
(c) 0–25% (particularly 5–15%) of a volatile silicone, (for example, a cyclomethicone such as a D5 cyclomethicone);
(d) 0–5% (particularly 0.1–2%) of a silicone elastomer (actives basis) (cyclomethicone carrier);
Internal Phase comprising:
(a) 0.1–25% of an antiperspirant active (on an anhydrous basis) (especially 7–25% for an antiperspirant or 0.1–5% for a deodorant);
(b) a sufficient amount of a glycol component such as propylene glycol to dissolve the antiperspirant active and to complete the internal phase;
(c) 0.5–15% (particularly 2–15%) water;
(d) 0–5% nonionic emulsifier (for example, Oleth-20);
(e) 0–3% NaCl (0–3% on a dry basis but added in a 20–30% water solution).

Formulation F:
Same as Formulation E but with the ester component being made with 0.5–14.5% (particularly 2–10%) C12–15 alkyl benzoate and 0.5–14.5% (particularly 2–10%) isostearyl stearate.

Formulation G:
Same as Formulation E but with the ester component being made with 0.5–14.5% (particularly 2–10%) C12–15 alkyl benzoate and 0.5–14.5% (particularly 2–10%) 2,6 diethylhexylnaphthalate.

Formulation H:
Same as Formulation E but with the ester component being made with 0.5–14.4% (particularly 5–10%) C12–15 alkyl benzoate; and 0.5–14.4% (particularly 5–10%) benzyl benzoate; and 1–5% (particularly 0.1–4%) octyl methoxy cinnamate.

Formulae I–P
Any of Formulae A–H where a water soluble salt, an aqueous solution of a water soluble salt or and ethanol/water solution of a water soluble salt is used instead of water. Examples with NaCl have been listed above, but specific salts also include $ZnCl_2$, zinc citrate, zinc gluconate magnesium sulfate, strontium lactate, sodium acetate, zinc acetate, and calcium chloride, particularly when the salt is added as a premixture of 10–30%, especially 25–30%, solution made with water, ethanol or a water/ethanol mixture.

Formulation I:
External Phase: Same as Formulation A.
Internal Phase comprising:
(a) 0.1–25% of an antiperspirant active (on an anhydrous basis) (especially 7–25% for an antiperspirant or 0.1–5% for a deodorant);
(b) a sufficient amount of a glycol component such as propylene glycol to dissolve the antiperspirant active and to complete the internal phase;
(c) 0.5–15% (particularly 2–5%) water;
(d) 0–5% nonionic emulsifier (for example, Oleth-20);
(e) 0–15% of a 30% $ZnCl_2$ water solution.

Formulation J:
  External Phase Same as Formulation B.
  Internal Phase comprising:
    (a) 0.1–25% of an antiperspirant active (on an anhydrous basis) (especially 7–25% for an antiperspirant or 0.1–5% for a deodorant),
    (b) a sufficient amount of a glycol component such as propylene glycol to dissolve the antiperspirant active;
    (c) 0.5–15% (particularly 2–5%) water;
    (d) 0–5% nonionic emulsifier (for example, Oleth-20);
    (e) 0–15% of a 10% zinc gluconate water solution.
Formulation K:
  External Phase Same as Formulation C.
  Internal Phase comprising:
    (a) 0.1–25% of an antiperspirant active (on an anhydrous basis) (especially 7–25% for an antiperspirant or 0.1–5% for a deodorant);
    (b) a sufficient amount of a glycol component such as propylene glycol to dissolve the antiperspirant active and to complete the internal phase;
    (c) 0.5–15% (particularly 2–5%) water;
    (d) 0–5% nonionic emulsifier (for example, Oleth-20);
    (e) 0–9% of a 30% $ZnCl_2$ ethanolic solution.
Formulation L:
  External Phase Same as Formulation D.
  Internal Phase comprising:
    (a) 0.1–25% of an antiperspirant active (on an anhydrous basis) (especially 7–25% for an antiperspirant or 0.1–5% for a deodorant);
    (b) a sufficient amount of a glycol component such as propylene glycol to dissolve the antiperspirant active and to complete the internal phase;
    (c) 0.5–15% (particularly 2–5%) water;
    (d) 0–5% nonionic emulsifier (for example, Oleth-20);
    (e) 0–9% of a 25% strontium lactate aqueous solution.
Formulation M:
  External Phase Same as Formulation E.
  Internal Phase comprising:
    (a) 0.1–25% of an antiperspirant active (on an anhydrous basis) (especially 7–25% for an antiperspirant or 0.1–5% for a deodorant);
    (b) a sufficient amount of a glycol component such as propylene glycol to dissolve the antiperspirant-active and to complete the internal phase;
    (c) 0.5–15% (particularly 2–5%) water;
    (d) 0–5% nonionic emulsifier (for example, Oleth-20);
    (e) 0–9% of a magnesium sulfate solution.
Formulation N:
  External Phase Same as Formulation F.
  Internal Phase comprising:
    (a) 0.1–25% of an antiperspirant active (on an anhydrous basis) (especially 7–25% for an antiperspirant or 0.1–5% for a deodorant);
    (b) a sufficient amount of a glycol component such as propylene glycol to dissolve the antiperspirant active and to complete the internal phase;
    (c) 0.5–15% (particularly 2–5%) water;
    (d) 0–5% nonionic emulsifier (for example, Oleth-20);
    (e) 0–9% of a sodium acetate aqueous solution.
Formulation O:
  External Phase Same as Formulation G.
  Internal Phase comprising:
    (a) 0.1–25% of an antiperspirant active (on an anhydrous basis) (especially 7–25% for an antiperspirant or 0.1–5% for a deodorant);
    (b) a sufficient amount of a glycol component such as propylene glycol to dissolve the antiperspirant active and to complete the internal phase;
    (c) 0.5–15% (particularly 2–5%) water;
    (d) 0–5% nonionic emulsifier (for example, Oleth-20);
    (e) 0–9% of a zinc acetate 10% aqueous solution.
Formulation P:
  External Phase Same as Formulation H
  Internal Phase comprising:
    (a) 0.1–25% of an antiperspirant active (on an anhydrous basis) (especially 7–25% for an antiperspirant or 0.1–5% for a deodorant);
    (b) a sufficient amount of a glycol component such as propylene glycol to dissolve the antiperspirant active and to complete the internal phase;
    (c) 0.5–15% (particularly 2–5%) water;
    (d) 0–5% nonionic emulsifier (for example, Oleth-20);
    (e) 0–9% of a 30% calcium chloride aqueous solution.
Formulations Q–X:
  Any of Formulae A–H where the composition comprises an additional ingredient of up to 10% ethanol which is substituted for a portion of the water content.
Formulation Y:
  External Phase comprising:
    (a) 0.5–25% (particularly 5–15%) of C12–15 alkyl benzoate;
    (b) 0.1–7% (particularly 3.0–6.0) of a 48% dimethicone copolyol in cyclomethicone) (or an equivalent amount of actives if other concentrations are used);
    (c) 0–25% (particularly 5–15%) of a volatile silicone (for example, a cyclomethicone such as a D5 cyclomethicone);
    (d) 0–5% (particularly 0.1–2%) of a silicone elastomer (actives basis) (cyclomethicone carrier);
  Internal Phase comprising:
    (a) 0.1–25% of an antiperspirant active (on an anhydrous basis) (especially 7–25% for an antiperspirant or 0.1–5% for a deodorant);
    (b) a sufficient amount of a glycol component such as propylene glycol to dissolve the antiperspirant active (for example, 35–55% of a glycol component for an antiperspirant product and 50–80% of a glycol component for a deodorant product);
    (c) 0.5–15% (particularly 2–5%) water;
    (d) 0–5% nonionic emulsifier (for example, Oleth-20);
    (e) 0–3% NaCl (0–3% on a dry basis but added in a 20–30% water solution); and
    (f) 0–12% alcohol (for example, 5–15% of 95% ethanol).
Formulation Z:
  External Phase comprising:
    (a) 0.5–25% (particularly 5–15%) of C12–15 alkyl benzoate;
    (b) 0.1–7% (particularly 6–12%) of a 25% dimethicone copolyol in cyclomethicone);
    (c) 0–25% (particularly 5–15%) of a volatile silicone (for example, a cyclomethicone such as a D5 cyclomethicone);
    (d) 0–5% (particularly 0.1–2%) of a silicone elastomer (actives basis) (cyclomethicone carrier);
  Internal Phase comprising:
    (a) 0.1–25% of an antiperspirant active (on an anhydrous basis) (especially 7–25% for an antiperspirant or 0.1–5% for a deodorant);
    (b) a sufficient amount of a glycol component such as propylene glycol to dissolve the antiperspirant active and to complete the internal phase;

(c) 0.5–15% (particularly 2–5%) water;
(d) 0–5% nonionic emulsifier (for example, Oleth-20);
(e) 0–3% NaCl (0–3% on a dry basis but added in a 20–30% water solution).

Formulation AA:
External Phase: Same as Formulation A
Internal Phase:
(a) 0.05–5.0% of an antibacterial agent
(b)–(e) same as Formulation A.

Formulation BB:
External Phase: Same as Formulation B
Internal Phase:
(a) 0.05–5.0% of an antibacterial agent
(b)–(e) same as Formulation B.

Formulation CC:
External Phase: Same as Formulation C
Internal Phase:
(b) 0.05–5.0% of an Antibacterial
(b)–(e) same as Formulation C.

Formulation DD:
External Phase: Same as formulation D
Internal Phase:
a) 0.05–5.0% of an antibacterial agent
(b)–(e) same as Formulation D.

While the mechanism of how this invention provides improved efficacy is not completely understood, it is believed that the invention solves two problems. The first problem is the barrier problem which is caused, in significant part, by the presence of a non-volatile silicone component. The second problem is the stability of the emulsion which, if too stable, results in failure of the antiperspirant to be released after application to the skin and a reduction in efficacy. This invention overcomes both of these problems with (a) the significant reduction (particularly not to exceed a level of 5% by weight) or, preferably, total elimination of the non-volatile silicone components that are frequently used in antiperspirant and/or deodorant products and (b) the creation of emulsion that exhibit satisfactory stability on the shelf and yet break down when applied to the skin to release the antiperspirant active allow for improved performance. As an additional benefit, the formulations of this invention may be made as clear products without the use of microemulsions.

The cosmetic composition according to the present invention can be packaged in conventional containers, using conventional techniques. Where a gel, cream or soft-solid cosmetic composition is produced, the composition can be introduced into a dispensing package (for example, conventional packages for gels with glide on applicators, jars where the gel or cream is applied by hand, and newer style packages having a top surface with pores) as conventionally done in the art. Thereafter, the product can be dispensed from the dispensing package as conventionally done in the art, to deposit the active material, for example, on the skin. For roll-ons the compositions can be placed in a conventional type of container. This provides good deposition of the active material on the skin.

Compositions of the present invention can be formulated as clear, translucent or opaque products, although clear products are preferred. A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear liquid or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400–800 nm through a sample 1 cm thick is at least 35%, preferably at least 50%. The gel or liquid is deemed translucent if the maximum transmittance of such light through the sample is between 2% and less than 35%. A gel or liquid is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Pat. No. Application Publication No. 291,334 A2. Thus, according to the present invention, there are differences between transparent (clear), translucent and opaque compositions.

Compositions of the present invention may be made by the techniques described in the Examples below. In general, the external and internal phases are formed separately using heating with the addition of a non-ionic emulsifier as needed. The alcohol component is added to the internal phase. The internal phase is added to the external phase very slowly. After the addition has been completed, the mixture is stirred at speeds on the order of 500–1000 rpm (for example, 1000 rpm), to achieve a homogeneous mixture, followed by homogenization at speeds which are correlated with a voltage setting of about 55–65, particularly 60, on a Powerstat Variable Autotransformer to achieve the target viscosity. Compositions with a viscosity of 0–50,000 centipoise, especially 5,000–20,000 centipoise, may be suitable for roll-on products while compositions having a viscosity on the order of 50–400,000 centipoise may be more suitable for soft solids or creams.

A variety of equipment and techniques may be used to obtain the compositions of the invention, including one pass homogenization, colloidal mill. Examples of such equipment include Sonic Production Sonolator 200-30, and Sonic Tri-Homo Colloid Mill both of which may be obtained from Sonic Corporation, Stratford, Conn.

It is believed that the more homogeneous the composition is and the more uniform the particle size, the better properties of the composition.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C unless otherwise indicated. The alcohol used was 95% unless otherwise indicated. Unless otherwise indicated, "water" or "D.I. water" mean deionized water. As is true throughout the application, the amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997). Viscosities are measured using Brookfield viscometers unless otherwise indicated. While specific amounts of particular elastomers have been described, there are chemical differences in the variety of elastomers that are available. The use of different elastomers may result in the need to increase or decrease the amount of elastomer used in a particular formulation, especially if a clear product is desired.

Example 1

General Method—No Elastomer

In general, the external and internal phases are formed separately either at room temperature or with heating as described below. The internal phase is added to the external phase very slowly while stirring at to form an emulsion. After the addition has been completed, the mixture is stirred at higher speed to achieve a homogeneous mixture. The final formula viscosity is then achieved by homogenizing the emulsion under either batch or continuous process conditions as described below. The fragrance may be added at any time during the process prior to final homogenization.

Preparation of External Phase:

The ingredients to be used in the external phase are weighed out at room temperature and combined in a suitable vessel such as a 2 liter glass beaker. The mixture is stirred at about 500 rpm for 15–20 minutes using an overhead mixer such as a Lightnin Mixer Model L1003. If a waxy or solid emollient is to be added to the external (also called "continuous") phase, the mixture may be heated to facilitate dissolution while stirring then cooled to room temperature prior to combination with the internal phase as described below.

Preparation of Internal Phase:

The internal dispersed phase is prepared as described below. Ingredients are mixed for a time sufficient to achieve homogeneity. The antiperspirant active used (for example, Westchlor A2Z4105 (28% aluminum-zirconium glycinate in propylene glycol)) is weighed into a large beaker equipped with an overhead stirrer. Other internal phase ingredients are then added while stirring.

The fragrance (if any is used) is added last and may be added either to the internal phase or the external phase or the final formula prior to homogenization. For many of the examples described here, one could add the fragrance to the internal phase.

If an optional non-ionic emulsifier such as Oleath-20 is used, the emulsifier and propylene glycol are combined in a separate beaker and heated to 40 degrees C with stirring until the non-ionic emulsifier completely dissolved. The heat is turned off and the remaining ingredients to be used in the internal phase, including the antiperspirant active are weighed out and added to the mixture of propylene glycol and non-ionic emulsifier.

If water or a salt solution are used, the internal phase is prepared as follows. The solution containing antiperspirant active salt as received from supplier is weighed into a large beaker equipped with a magnetic stirrer. Additional ingredients such as propylene glycol, ethanol and water are added while stirring. If a salt water solution is used (such as for NaCl, etc.), the salt water solution is prepared by dissolving the crystalline salt in water in a separate beaker and stirring until dissolved. The salt water solution is then added to the rest of the internal phase and the mixture is stirred until homogeneous.

Preparation of the Emulsion:

The internal phase made as described above is then added to the external phase over the course of 15–30 minutes while stirring at a speed of 500–1000 RPM. After the addition is complete, the mixture is stirred at 1000–1300 rpm for 20 minutes using a Lightnin Mixer Model L1003. The mixture is then homogenized for 2–4 minutes using a homogenizer from Greerco Corp., Hudson, N.H. at a reading of about 60 on a Powerstat Variable Autotransformer from Superior Electric Co., Bristol, Conn.

Further Processing:

The product is then further processed by homogenized to achieve the desired final viscosity. This can be done by using a Gilford-Wood Model 1-L (Greerco Corp., Hudson, N.H.) homogenizer. The homogenizer speed is controlled by a Powerstat Variable Autotransformer Type 3PN116B (Superior Electronic. Co., Bristol, Conn.). Typical voltage setting and processing time are chosen to give a desired final formula viscosity.

An other method of homogenization of the final product is to pass the emulsion through a colloid mill such as a Sonic Tri-Homo Colloid Mill or a process sonolator such Sonic Production Sonolator 200-30 both available from Sonic Corporation of Stratford, Conn. Process conditions are chosen to give the desired final product viscosity.

Example 1B

Evaluation of Viscosity

Brookfield Viscosity

Viscosity can be measured using a Brookfield instrument (Model DV11+) with an E Spindle at 2.5 revolutions per minute (rpm) and a setting of S 95. Units are in centipoise ("cps").

Carri-Med Viscosity

A second way of evaluating rheology is with the use of Carri-Med equipment to obtain complex viscosity. Rheological parameters can be measured using a Carri-Med CSL 100 instrument with parallel plates. Initially the zero gap is set on the instrument. A sample of approximately 5 grams is placed on the stage of the instrument. A 15 minute compression is used for sample equilibration. The excess of the sample is scraped around the plate geometry. The Theological parameters G, G", tan (delta) and complex viscosity (n*) can be measured by torque sweep experiments. An acrylic plate 6 cm in diameter can be used. A gap (1000 microns) is used between the two plates. Temperature is maintained at 23 degrees C. The oscillation stress can be varied from 2.358 Pa to 50.74 Pa with an oscillation frequency kept constant at 1 Hertz. Units are in Pascal seconds ("Pa sec").

Example 2

General Method With Elastomer

The Method of Example 1 can be repeated with the addition of an elastomer component. The elastomer component is obtained as a suspension of elastomer in cyclomethicone (for example at a concentration of 5.8% active in D5 cyclomethicone). The elastomer component is added to the external phase with stirring at high speed (800–1000 rpm for a 1 kilogram batch) until no particles of elastomer are visible to the eye.

Examples 3–6

The method of Example 1 is repeated with the types and amounts of ingredients listed in Table I. Viscosity measurements can be obtained using the methods described in Example 1 to obtain the data as listed in Table I.

TABLE I

| Ingredient | Ex. 3 | Ex. 4 | Ex. 5 | Ex. 6 | Ex. 7 |
|---|---|---|---|---|---|
| Cyclomethicone and dimethicone copolyol (48%) DC 2-5185C | 3.75 | 3.75 | 6.0 | 6.0 | 3.75 |
| Cyclomethicone (D5) | 9.75 | 7.75 | 11.1 | 11.8 | 9.75 |
| C12–15 alkyl benzoate | 10.5 | 10.5 | 13.7 | 13.7 | 10.5 |
| Dimethiconol[a] | 0 | 2.0 | 0 | 0 | 0 |
| Al—Zr gly in propylene glycol (28%) | 54.0 | 54.0 | 53.57 | 53.57 | 54.0 |
| Propylene glycol | 8.0 | 8.0 | 0 | 1.3 | 8.0 |
| SD Alcohol 40 (95%) | 9.0 | 9.0 | 0 | 0 | 0 |
| Water | 4.0 | 4.0 | 12.13 | 12.13 | 11.0 |
| NaCl[b] | 0 | 0 | 2.0 | 0 | 0 |
| Fragrance | 1.0 | 1.0 | 1.0 | 1.0 | 1.0 |
| Oleth-20 | 0 | 0 | 0.5 | 0.5 | 0 |
| Urea | 0 | 0 | 0 | 0 | 2.0 |
| Initial complex viscosity[c] (Pa Sec) | 200–220 | 200–220 | 200–220 | 120–135 | n.d. |
| Complex Viscosity[c] (after 4 weeks @ 49° C.) (Pa sec) | 200–220 | 200–220 | 155–170 | 70–80 | n.d. |
| Conductivity[d] | 1884 | 1985 | >1000 | n.d. | n.d. |

[a]= Silicone DC 1501 Fluid (long chain polysiloxane).
[b]= NaCl and water are premixed and added together.
[c]= CarriMed technique to be used for complex viscosities.
[d]= Standard Test as described above with units in micro Siemens.

Examples 8–11

The method of Example 1 may be repeated with the types and amounts of ingredients listed in Table II. Viscosity measurements can be obtained using the methods described in Example 1 to obtain the data as listed in Table II.

TABLE II

| Ingredient | Ex. 8 | Ex. 9 | Ex. 10 | Ex. 11 |
|---|---|---|---|---|
| Cyclomethicone and dimethicone copolyol (48%) DC 2185C | 5.15 | 5.15 | 5.06 | 5.06 |
| Cyclomethicone (D5) | 8.75 | 8.75 | 8.01 | 8.01 |
| C12–15 alkyl benzoate | 11.1 | 11.1 | 11.29 | 11.12 |
| Al—Zr gly in propylene glycol (28%) | 59.57 | 59.57 | 58.13 | 58.13 |
| Propylene glycol | 0 | 0 | 0 | 2.21 |
| SD Alcohol 40 (95%) | 0 | 0 | 0 | 0 |
| Water[a] | 11.93 | 12.43 | 13.16 | 13.16 |
| NaCl[a] | 2.0 | 2.0 | 2.0 | 0 |
| Fragrance | 1.0 | 1.0 | 1.0 | 1.0 |
| Oleth-20 | 0.5 | 0 | 0.54 | 0.5 |
| Dimethicone (100 centistokes) | 0 | 0 | 0.81 | 0.81 |
| Initial complex viscosity[b] (Pa sec) | n.d. | n.d. | 200–215 | 105–115 |
| Conductivity[c] | n.d. | n.d. | n.d. | 1623 |

[a]= NaCl and water are premixed and added together.
[b]= CarriMed technique to be used for complex viscosities.
[c]= Standard Test as described above with units in micro Siemens.

Examples 16–19

The method of Example 1 may be repeated with the types and amounts of ingredients listed in Table III. Viscosity measurements can be obtained using the methods described in Example I to obtain the data as listed in Table III.

TABLE III

| Ingredient | Ex. 16 | Ex. 17 | Ex. 18 | Ex. 19 |
|---|---|---|---|---|
| Cyclomethicone and dimethicone copolyol (48%) DC 2185C | 3.75 | 3.75 | 3.75 | 6.0 |
| Cyclomethicone (D5) | 10.25 | 10.25 | 9.25 | 11.1 |
| C12–15 alkyl benzoate | 0 | 5.0 | 0 | 13.7 |
| Benzyl benzoate | 10.0 | 5.0 | 0 | 0 |
| Isostearyl isostearate | 0 | 0 | 11.0 | 0 |
| Al—Zr gly in propylene glycol (28%) | 54.0 | 54.0 | 54.0 | 53.57 |
| Propylene glycol | 8.0 | 8.0 | 8.0 | 0 |
| SD Alcohol 40 (95%) | 9.0 | 9.0 | 9.0 | 0 |
| Water[a] | 4.0 | 4.0 | 4.0 | 11.13 |
| ZnCl$_2$[a] | 0 | 0 | 0 | 3.0 |
| Fragrance | 1.0 | 1.0 | 1.0 | 1.0 |
| Oleth-20 | 0 | 0 | 0 | 0.5 |

[a]= ZnCl$_2$ and water are premixed and added together.

Examples 20–23

The method of Example 1 may be repeated with the types and amounts of ingredients listed in Table IV. Viscosity measurements can be obtained using the methods described in Example 1 to obtain the data as listed in Table IV.

TABLE IV

| Ingredient | Ex. 20 | Ex. 21 | Ex. 22 | Ex. 23 |
|---|---|---|---|---|
| Cyclomethicone and dimethicone copolyol (48%) | 6.0 | 6.0 | 5.0 | 5.5 |
| Cyclomethicone (D5) | 9.1 | 9.1 | 8.8 | 9.1 |
| C12–15 alkyl benzoate | 11.4 | 10.4 | 10.2 | 10.4 |
| Al—Zr gly in propylene glycol (28%) | 58.07 | 57.57 | 53.57 | 58.57 |
| Propylene glycol | 3.93 | 0.5 | 0.43 | 4.43 |
| SD Alcohol 40 (95%) | with ZnCl$_2$ | 0 | 9.0 | with ZnCl$_2$ |
| Water | 0 | with ZnCl$_2$ | with ZnCl$_2$ | 0 |
| ZnCl$_2$ (20% in water) | 0 | 14.93 | 12.0 | 0 |
| ZnCl$_2$ (18.1% in 95% ethanol) | 11.0 | 0 | 0 | 11.0 |
| Fragrance | 1.0 | 1.0 | 1.0 | 1.0 |
| Oleth-20 | 0.5 | 0.5 | 0 | 0 |

Examples 24–27

The method of Example 1 may be repeated with the following amounts of ingredients listed in Table V may be used to make compositions according to the invention.

TABLE V

| Ingredient | Ex. 24 | Ex. 26 | Ex. 27 | Ex. 25A | Ex. 25B | Ex. 25C |
|---|---|---|---|---|---|---|
| Cyclomethicone and dimethicone copolyol (40%) | 5.00 | 4.06 | 4.15 | 5.25–5.75 | 5.25–5.75 | 5.25–5.75 |
| Cyclomethicone (D5) | 12.1 | 9.01 | 9.75 | 8.25–8.75 | 8.25–8.75 | 8.25–8.75 |
| C12–15 alkyl benzoate | 13.7 | 11.12 | 11.10 | 11.00 | 11.00 | 11.00 |
| Al—Zr gly in propylene glycol (28%)[a] | 53.57 | 58.13 | 59.57 | 59.00 | 59.00 | 59.00 |
| Propylene glycol | 0 | 0 | 0 | 2.00 | 6.00 | 2.00 |
| SD Alcohol 40 (95%) | 0 | 0 | 0 | 0 | 9.00 | 9.00 |
| Water | 12.13 | 13.16 | 11.93 | 13.00 | 0 | 4.00 |
| NaCl | 2.0 | 2.17 | 2.00 | 0 | 0 | 0 |
| Fragrance | 1.0 | 1.0 | 1.0 | 1.0 | 1.0 | 1.0 |
| Oleth-20 | 0.5 | 0.54 | 0.5 | 0 | 0 | 0 |
| Dimethicone (Dow Corning 200 Fluid (50 centistokes) | 0 | 0.81 | 0 | 0 | 0 | 0 |
| Initial complex viscosity (CarriMed) | 210–220 Pa sec | 125–135 Pa sec | n.d. | 170–180 Pa sec | 90–100 Pa sec | 100–110 Pa sec |
| Complex Viscosity (after 2 weeks at 49° C.) | n.d. | n.d. | n.d. | 90–100 Pa sec | 40–45 Pa sec | 115–130 Pa sec |
| Complex Viscosity (after 4 weeks at 49° C.) | 280–295 Pa sec | n.d. | n.d. | 70–80 Pa sec | 65–70 Pa sec | 170–180 Pa sec |
| Conductivity | 727 | 819 | n.d. | n.d. | n.d. | n.d. |

[a] = Westchlor 4105 used for Examples 25 A–C.

Examples 28–34

The method of Example 1 may be used to make compositions using the following ingredients as shown in Table VI. The items listed above the antiperspirant active are used for the external phase and the ingredients from the antiperspirant ingredient down are used for the internal phase. Batches can be made in 500 g quantities.

Examples 35–40

The method of Example 1 may be used to make compositions using the following ingredients as shown in Table VII. The items listed above the antiperspirant active are used for the external phase and the ingredients from the antiperspirant ingredient down are used for the internal phase. Batches can be made in 500 g quantities.

TABLE VI

| Ingredient | Ex. 28 | Ex. 29 | Ex. 30 | Ex. 31 | Ex. 32 | Ex. 33 | Ex. 34 |
|---|---|---|---|---|---|---|---|
| C12–15 alkyl benzoate[a] | 10.40 | 10.00 | 9.10 | 9.25 | 8.25 | 9.25 | 9.30 |
| Cyclomethicone (D5) | 7.10 | 7.50 | 10.90 | 8.75 | 9.75 | 8.75 | 8.20 |
| Neopentyl glycol diheptanoate | 0 | 2.00 | | 4.00 | 2.00 | 4.00 | 0 |
| PEG-8 laurate[e] | 0 | 0 | 2.00 | 0 | 0 | 0 | 0 |
| Isocetyl stearate[h] | 0 | 0 | 0 | 0 | 2.00 | 0 | 0 |
| Dimethicone copolyol laurate[i] | 0 | 0 | 0 | 0 | 0 | 0 | 2.00 |
| 40% dimethicone copolyol (in cyclomethicone) | 5.50 | 5.50 | 3.00 | 3.00 | 3.00 | 3.00 | 5.50 |
| Antiperspirant active[b] | 59.00 | 59.00 | 59.00 | 53.50 | 59.00 | 59.00 | 59.00 |
| Water | 13.00 | 13.00 | 13.00 | 4.00 | 13.00 | 4.00 | 13.00 |
| PPG-12-buteth-16[c] | 4.00 | 0 | 0 | 0 | 0 | 0 | 0 |
| Propylene glycol | 0 | 2.00 | 2.00 | 0 | 2.00 | 2.00 | 2.00 |
| Tripropylene glycol | 0 | 0 | 0 | 4.50 | 0 | 0 | 0 |
| Ethanol (95%) | 0 | 0 | 0 | 9.00 | 0 | 9.00 | 0 |
| Cosmetic wax[g] | 0 | 0 | 0 | 3.00 | 0 | 0 | 0 |
| Fragrance[d] | 1.00 | 1.00 | 1.00 | 1.00 | 1.00 | 0 | 1.00 |
| Initial viscosity[f] | | | | | | | |

[a] = FINSOLV TN.
[b] = WESTCHLOR A2Z 4105 (28% propylene glycol and 5.5% glycine).
[c] = UCON 50-660 from Amerchol Corp.
[d] = Add as a separate ingredient to either phase or at the end.
[e] = JEEMATE 400ML from Jeen International Corp.
[f] = Brookfield method as described above will give values in the range of 160,000–230 centipoise.
[g] = DOW CORNING 2501 cosmetic wax (dimethicone copolyol).
[h] = Crodanol ICS from Croda, Inc.
[i] = SILWAX WSL from Siltech Corp.

TABLE VII

| Ingredient | Ex. 35 | Ex. 36 | Ex. 37 | Ex. 38 | Ex. 39 | Ex. 40 |
|---|---|---|---|---|---|---|
| C12–15 Alkyl benzoate[a] | 7.70 | 9.00 | 7.30 | 12.00 | 10.40 | 7.90 |
| Cyclomethicone[b] | 4.30 | 10.00 | 7.70 | 10.00 | 9.80 | 15.10 |
| Neopentyl glycol diheptanoate | 8.00 | 4.00 | 0 | 0 | 0 | 0 |
| PPG-10-cetyl ether[f] | 0 | 0 | 5.00 | 3.00 | 0 | 0 |
| Dimethicone[g] (50 centistokes) | 0 | 0 | 0 | 0 | 0.80 | 1.00 |
| 40% dimethicone copolyol (in cyclomethicone) | 5.00 | 6.00 | 5.00 | 5.00 | 4.00 | 5.00 |
| Antiperspirant active[c] | 59.00 | 35.72 | 59.00 | 50.00 | 59.00 | 54.00 |
| Water | 3.00 | 0 | 13.00 | 12.70 | 13.00 | 0 |
| NaCl[h] | 0 | 0 | 0 | 2.00 | 0 | 0 |
| Propylene glycol | 0 | 7.15 | 2.00 | 3.80 | 2.00 | 16.00 |
| Tripropylene glycol | 2.00 | 17.51 | 0 | 0 | 0 | 0 |
| Ethanol (95%) | 10.00 | 9.12 | 0 | 0 | 0 | 0 |
| Polysorbate 80 | 0 | 0.50 | 0 | 0 | 0 | 0 |
| Oleth-20 | 0 | 0 | 0 | 0.50 | 0 | 0 |
| Fragrance[d] | 1.00 | 1.00 | 1.00 | 1.00 | 1.00 | 1.00 |
| Initial viscosity[e] | 220,000 | 230,000 | 110,000 | 200,000 | 300,000 | 170,000 |

[a]= FINSOLV TN.
[b]= Dow Corning 245.
[c]= WESTCHLOR A2Z 4105 (28% propylene glycol and 5.5% glycine) for Examples 35, 37 and 39; WESTCHLOR ZR 40BX3 (42% ACT, 29% propylene glycol and 29% water) for Example 36; WESTCHLOR 35B (30% propylene glycol and 5.1% glycine) for Example 38; and REZAL 36 GP for Example 40.
[d]= Add as a separate ingredient to either phase or at the end.
[e]= Brookfield method as described above. Unit is centipoise.
[f]= PROCETYL 10 from Croda.
[g]= DOWCORNING 200 Fluid.
[h]= NaCl is premixed with water in Ex. 38 before addition.

Examples 45–48

The method of Example 2 may be used to make compositions using the following ingredients as shown in Table VIII. The items listed above the antiperspirant active are used for the external phase and the ingredients from the antiperspirant ingredient down are used for the internal phase. Batches can be made in 500 g quantities.

TABLE VIII

| Ingredient | Ex. 45 | Ex. 46 | Ex. 47 | Ex. 48 |
|---|---|---|---|---|
| C12–15 Alkyl benzoate[a] | 7.25 | 6.90 | 6.35 | 0 |
| Cyclomethicone[b] | 6.75 | 7.10 | 7.65 | 4.00 |
| Triethylhexanoin[f] | 4.00 | 0 | 0 | 0 |
| Ethyl hexyl isostearate[h] | 0 | 0 | 0 | 0 |
| Silicone elastomer in cyclomethicone[g] | 6.00 | 6.00 | 6.00 | 8.00 |
| Glyceryl oleate in propylene glycol[i] | 0 | 0 | 4.00 | 0 |
| Neopentyl glycol diheptanoate | 0 | 0 | 0 | 4.00 |
| Isopropyl isostearate | 0 | 0 | 0 | 8.00 |
| 40% dimethicone copolyol (in cyclomethicone) | 5.00 | 5.00 | 5.00 | 5.00 |
| Antiperspirant active[c] | 35.00 | 35.00 | 35.00 | 32.15 |
| Water | 0 | 0 | 0 | 6.62 |
| Propylene glycol | 17.00 | 17.00 | 17.00 | 0 |
| Tripropylene glycol | 8.25 | 8.25 | 8.25 | 21.00 |
| Ethanol (95%) | 9.52 | 9.52 | 9.52 | 10.00 |
| Polysorbate 80 | 0.23 | 0.23 | 0.23 | 0.23 |
| Fragrance[d] | 1.00 | 1.00 | 1.00 | 1.00 |
| Initial viscosity[e] | | | | |

[a]= FINSOLV TN.
[b]= Dow Corning 245.
[c]= WESTCHLOR A2Z 4105 (28% propylene glycol and 5.5% glycine) for Example 48; and WESTCHLOR ZR 40BX3 (42% ACT, 29% propylene glycol and 29% water) for Examples 45–47
[d]= Add as a separate ingredient to either phase or at the end.
[e]= Brookfield method as described above and will give values in the range of 180,000–220,000 centipoise.
[f]= ESTOL 3609 from Uniquema.
[g]= Elastomer as described in U.S. Pat. 6,060,546 at a concentration of 5.8% solids in cyclomethicone. This patent is incorporated by reference for the description of the elastomer.
[h]= PRISORINE 2036 from Uniquema.
[i]= ARLACEL 186 from Uniquema.

We claim:
1. A low water emulsion made by combining 15–33% of an external phase and 67–85% of an internal phase wherein:
(I) the external phase comprises:
(a) 1–25% of an organic ester having a refractive index in the range of 1.43–1.60 and which allows the release of an antiperspirant active;
(b) a sufficient amount of a silicone copolyol to achieve a solids content of 0.25–10%, wherein the silicone copolyol may be added with or without solvent;
(c) a sufficient amount of a volatile silicone to achieve a quantum sufficient amount of the external phase as 15–33%;
(d) 0–5% of a silicone elastomer (on an actives basis); and
(e) 0–15% of at least one emollient.

(II) the internal phase comprises:
   (a) an effective amount of at least one cosmetically active ingredient selected from the group consisting of 0.1–25% of an antiperspirant active (on an anhydrous basis), 0.1–3% of a fragrance, and 0.05–5% of an antimicrobial;
   (b) a sufficient amount of a solvent component to dissolve the cosmetically active ingredient and to complete the internal phase up to a maximum of 80% of solvent;
   (c) 0.5–15% of water optionally containing up to 30% of an ionizable salt soluble in water;
   (d) 0–5% of a non-ionic emulsifier; and
   (e) 0–10% ethanol;
wherein: the final refractive index of the composition is in the range of 1.42–1.52; and all amounts are in percent by weight based on the entire weight of the composition.

2. A low water emulsion as claimed in claim 1 wherein the minimum conductance at least 250 micro Siemens/cm/ml at a loading of at least 7% by weight level of antiperspirant active.

3. A low water emulsion as claimed in claim 1 wherein the minimum conductance is at least 300 micro Siemens/cm/ml at a loading of at least 7% by weight level of antiperspirant active.

4. A low water emulsion as claimed in claim 1 wherein the minimum conductance is at least 400 micro Siemens/cm/ml at a loading of at least 7% by weight level of antiperspirant active.

5. A low water emulsion as claimed in claim 1 wherein the organic ester is selected from the group consisting of esters of formula R"—CO(O)—R', where each of R' and R" is independently selected from the group consisting of (a) C1–C30-straight and branched chain alkyls and alkenyls; and (b) an aromatic group such as phenyl, benzyl, naphthyl, or biphenyl wherein the aromatic is optionally substituted by one or more or the groups listed in (a), but provided that the total of the carbons for R'+R" is in the range of 8–30.

6. A low water emulsion as claimed in claim 1 wherein the organic ester is selected from the group consisting of C12–15 alkyl benzoate; octyl methoxy cinnamate in amounts less than 6%; isostearyl isostearate; benzyl benzoate; 2,6-di-(ethylhexyl)naphthalate; butyl octyl salicylate; glyceryl monostearate; n-dibutyl sebacate; isopropyl myristate; isopropyl palmitate; butyl stearate; cetyl lactate; isocetyl stearate; hexyl laurate; decyl oleate; isostearyl isostearate; ethyl hexyl maleate; sorbitan monoaurate; sorbitan monooleate; sorbitan sesquioleate; sorbitan trioleate; isopropyl palmitate; isopropyl stearate; stearyl stearate; diisopropyl adipate; diisopropyl sebacate; butyl myristate; and isopropyl laurate.

7. A low water emulsion as claimed in claim 1 comprising a sufficient amount of a silicone copolyol to achieve a solids content of 1.0–3.0%.

8. A low water emulsion as claimed in claim 1 wherein a refractive index is obtained for each of the external and internal phases and the refractive indices of the external and internal phases are matched within 0.01 to obtain a clear product.

9. A low water emulsion as claimed in claim 1 wherein the emulsion is an antiperspirant.

10. A low water emulsion as claimed in claim 1 wherein the emulsion is a deodorant.

11. A low water emulsion as claimed in claim 1 comprising up to 30% of an ionizable salt soluble in water.

12. A low water emulsion as claimed in claim 11 wherein the ionizable salt is selected from the group consisting of salts of the form $M_aX_b$ where a=1 or 2; b=1 or 2; M is a member selected from the group consisting of $Na^{+1}$, $Li^{+1}$, $K^{+1}$, $Mg^{+2}$, $Ca^{+2}$, $Sr^{+2}$, $Sn^{+2}$, and $Zn^{+2}$; and X is a member selected from the group consisting of chloride, bromide, iodide, citrate, gluconate, lactate, glycinate, glutamate, ascorbate, aspartate, nitrate, phosphate, hydrogenphosphate, dihydrogenphosphate, formate, malonate, maleate, succinate, carbonate, bicarbonate, sulfate and hydrogensulfate.

13. A low water emulsion as claimed in claim 12 wherein the ionizable salt is selected from the group consisting of NaCl, KCl, $ZnCl_2$, zinc citrate and zinc glycinate.

14. A low water emulsion as claimed in claim 1 further comprising up to 5% of a non-ionic emulsifier.

15. A low water emulsion as claimed in claim 1 further comprising up to 10% of ethanol.

16. A low water emulsion as claimed in claim 1 wherein refractive index of the emulsion is in the range of 1.42–1.52.

17. A low water emulsion as claimed in claim 1 wherein the solvent is a glycol or polyglycol selected from the group consisting of ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof.

18. A low water emulsion as claimed in claim 17 wherein the solvent is a glycol or polyglycol selected from the group consisting one or more members of the group consisting of propylene glycol, dipropylene glycol, tripropylene glycol, 2-methyl-1,3-propanediol, methyl propylene glycol, low molecular weight (less than 600) polyethylene glycol, low molecular weight (less than 600) polypropylene glycols, and mixtures of any of the foregoing.

19. A low water emulsion as claimed in claim 1 wherein the antimicrobial agent is selected from the group consisting of bacteriostatic quaternary ammonium compounds; 2,4,4'-trichloro-2'-hydroxydiphenylether; N-(4-chlorophenyl)-N'-(3,4-dichlorophenyl)urea; silver halides; octoxyglycerin and bacteriostatic zinc salts.

20. A low water emulsion as claimed in claim 9 wherein
   (I) the external phase comprises:
      (a) 5–15% of the organic ester;
      (b) 3.0–6.0 of a 48% dimethicone copolyol or its equivalent;
      (c) 5–15% of a volatile silicone;
      (d) 0–5% of a silicone elastomer (actives basis);
   (II) the internal phase comprises:
      (a) 7.0–25% of an antiperspirant active (on an anhydrous basis);
      (b) 35–55% of a solvent component which comprises at least one glycol;
      (c) 2–13% water;
      (d) 0–5% nonionic emulsifier;
      (e) 0–3% NaCl;
      (f) 0–10% ethanol or its equivalent; and
      (g) 0–3% fragrance.

21. A low water emulsion as claimed in claim 10 wherein
   (I) the external phase comprises:
      (a) 5–15% of the organic ester;
      (b) 3.0–6.0 of a 48% dimethicone copolyol or its equivalent;

(c) 5–15% of a volatile silicone;
(d) 0–5% of a silicone elastomer (actives basis);

(II) the internal phase comprises:
(a) up to 7.0% of an antiperspirant active (on an anhydrous basis);
(b) 40–80% of a solvent component which comprises at least one glycol;
(c) 2–13% water;
(d) 0–5% nonionic emulsifier;
(f) 0–3% NaCl;
(g) 0–10% ethanol;
(h) 0–3% fragrance.

22. A low water emulsion as claimed in claim 20 or claim 21 wherein the organic ester is C12–15 alkyl benzoate.

23. A low water emulsion as claimed in claim 20 or claim 21 comprising 2–7% water.

24. A low water emulsion as claimed in claim 1 or claim 11 wherein the internal phase additionally comprises a member selected from the group consisting of urea, guanidine hydrochloride, xylitol, trehalose, maltose and glycerine.

\* \* \* \* \*